(12) United States Patent
Joyce et al.

(10) Patent No.: US 6,846,946 B2
(45) Date of Patent: Jan. 25, 2005

(54) PROCESS FOR MAKING ORGANIC PRODUCTS AND IMPROVING THE QUALITY OF NON-PRODUCT STREAMS USING PHASE TRANSFER CATALYSIS

(75) Inventors: Peter J. Joyce, Mullica Hill, NJ (US); Roman Bielski, Coopersburg, PA (US); Marc Halpern, Cherry Hill, NJ (US)

(73) Assignee: Value Recovery, Inc., Bridgeport, NJ (US)

( * ) Notice: Subject to any disclaimer, the term of this patent is extended or adjusted under 35 U.S.C. 154(b) by 0 days.

(21) Appl. No.: 10/236,382

(22) Filed: Sep. 6, 2002

(65) Prior Publication Data

US 2003/0158435 A1 Aug. 21, 2003

Related U.S. Application Data

(60) Provisional application No. 60/397,433, filed on Jul. 19, 2002, and provisional application No. 60/357,666, filed on Feb. 15, 2002.

(51) Int. Cl.$^7$ .................... C07C 255/00; C07C 247/04; C07C 69/76
(52) U.S. Cl. .................... 558/388; 558/435; 552/6; 552/10; 560/8; 560/74; 560/129; 570/261
(58) Field of Search .................... 558/388, 435; 560/8, 74, 124; 552/6, 10; 570/261

(56) References Cited

U.S. PATENT DOCUMENTS

| | | | |
|---|---|---|---|
| 3,992,432 A | 11/1976 | Napier et al. | |
| 4,479,903 A | 10/1984 | Dauplaise | |
| 5,235,077 A | 8/1993 | Amini et al. | |
| 5,242,996 A | 9/1993 | Yamada et al. | |
| 5,483,007 A | 1/1996 | Johnson | |
| 5,554,753 A | 9/1996 | O'Donnell et al. | |
| 5,705,667 A | 1/1998 | De Haen et al. | |
| 5,731,460 A | 3/1998 | Johnstone et al. | |
| 6,051,725 A | 4/2000 | Crivello et al. | |
| 6,080,858 A | 6/2000 | Schumacher | |
| 6,596,870 B2 * | 7/2003 | Pochapsky et al. | 546/136 |

OTHER PUBLICATIONS

Kang et al., 2000, "Synthesis of benzyl cyanide with phase trnasfer catalyst.", CAS:133:209624.*

Qian et al, 2001, "Preparation of oxa(thia)diazolypyridine-one derivs . . . ", CAS:135:122510.*

Li et al., 1993, "Phase–transfer–catalyst synthesis of benzyl acetate from benzyl chloride and sodium acetate.", CAS:118:212695.*

Domenico Albanese; Dario Landini; Angelamaria Maia; and Michele Penso, "Key Role of Water for Nucleophilic Substitutions in Phase–Transfer–Catalyzed Processes: A Mini–Review," *Ind. Eng. Chem. Res.*, vol. 40, No. 11, 2001, pp. 2396–2401.

Peter Joyce, "Recovering value from byproducts using phase–transfer catalysis," *Chemical Innovation*, vol. 31, No. 9, Sep. 2001, pp. 42–44.

"Using Phase Transfer Catalysis to Clean Up Waste Streams," *Phase Transfer Catalysis Communications*, vol. 2, Issue 3, ©1996 PTC Communications, Inc., pp. 40, 41, and 46.

Jean Jacques Vanden Eynde and Isabelle Mailleux, "Quaternary Ammonium Salt–Assisted Organic Reactions in Water: Alkylation of Phenols," *Synthetic Communications*, vol. 31, Issue 1, 2000, pp. 1–7.

Ho–Shing Wu and Jaw–Jiun Lai, "Phenoxide Allylation in a Phase Transfer Catalytic Extracton System," *Ind. Eng. Chem. Res.*, vol. 34, Issue 5, 1995, pp. 1536–1538.

V. K. Krishnakumar and Man Mohan Sharma, "A Novel Method of Recovering Phenolic Substances from Aqueous Alkaline Waste Streams," *Ind. Eng. Chem. Process Des. Dev.*, vol. 23, No. 2, 1984, pp. 410–413.

Narendra N. Dutta, Somiran Borthakur, and Rasna Baruah, "A novel process for recovery of phenol from alkaline wastewater: laboratory study and predesign cost estimate," *Water Environment Research*, vol. 70, No. 1, Jan./Feb. 1998, pp. 4–9.

Charles M. Starks, "Phase–Transfer Catalysis. I. Heterogeneous Reactions Involving Anion Transfer by Quaternary Ammonium and Phosphonium Salts," *Journal of the American Chemical Society*, vol. 93, Issue 1, 1971, pp. 195–199.

Y. Sasson, R. Neumann, "Handbook of Phase Transfer Catalysis," Blackie Academic & Professional (unit of Chapman and Hall), 1$^{st}$ Edition, 1997, pp. 191–192.

C. M. Starks, C. L. Liotta, and M. Halpern, "Phase–Transfer Catalysis: Fundamentals, Applications and Industrial Perspectives," *Chapman and Hall: New York, 1994*, pp. 622–625.

(List continued on next page.)

*Primary Examiner*—Rita Desai
*Assistant Examiner*—Robert Shiao
(74) *Attorney, Agent, or Firm*—RatnerPrestia

(57) ABSTRACT

A method for preparing organic products from aqueous solutions, such as waste or byproduct liquid streams and waste or byproduct gas or vapor streams, uses phase transfer catalysis to transfer a chemical species in low concentration from the aqueous solution to the organic phase or the aqueous-organic interface. The system has little or no organic solvent, and the organic phase contains an electrophile which participates in the reaction. In one embodiment, the aqueous solution is contacted with the electrophile and a phase transfer catalyst and, optionally, a pH adjusting agent in the event that the chemical species in the aqueous solution is not sufficiently ionized to react with the electrophile, and optionally an organic solvent. A method for continuously converting a chemical species involves this contacting step, separating the phases, then dividing the organic phase into the product, the phase transfer catalyst, and the optional organic solvent.

18 Claims, 1 Drawing Sheet

OTHER PUBLICATIONS

CA107(26):249D83h of Minoru Tanaka: Hiroshi Takigawa; Yuta Yasaka; Toshiyuki Shono; Koichi Funazo; and Hsin-Lung Wu, Derivation of inorganic anions with pentafluorobenzyl methanesulphonate for gas chromatography, *Journal of Chromatography A*, vol. 404, 1987, pp. 175–182 (Abstract Only).

CA110(3):23359c of Japanese Patent No. 63–196548 for "Preparation of suberonitrile by two–step cyanation of 1.6–dichlorohexand eith recycled sodium cyanide," by Hiroyaki Nanba; Noriko Takahashi; Koichi Abe; and Masac Saito (Mitsubishi Gas Chemical Co., Inc.) (Abstract Only).

E. M. Asatryan; G. S. Grigoryan; A. Ts. Malkhasyan; and G. T. Martirosyan, "Dehydrochlorination of chlororganic compounds in chloroprene production wastes under conditions of phase–transfer catalysis." (Abstract Only).

* cited by examiner

PROCESS FOR MAKING ORGANIC PRODUCTS AND IMPROVING THE QUALITY OF NON-PRODUCT STREAMS USING PHASE TRANSFER CATALYSIS

This application claims benefit of 60/397,433 filed on Jul. 19, 2002, and claims benefit of 60/357,666 filed on Feb. 15, 2002.

STATEMENT REGARDING FEDERALLY SPONSORED RESEARCH OR DEVELOPMENT

This invention was made with Government support under Small Business Innovation Research (SBIR) grant application number 55118-99-1 awarded by the Department of Energy under DOE grant number DE-FG 02-99ER82864. The Government has certain rights in this invention.

FIELD OF THE INVENTION

The present invention pertains to the preparation of organic products from aqueous solutions and from gas and liquid organic streams, including non-product liquid streams, using phase transfer catalysis (PTC). The present invention also pertains to improving the quality of non-product streams.

BACKGROUND OF THE INVENTION

Phase transfer catalysts are used in a wide variety of chemical processes where one or more phase boundaries exist and one or more constituents cross a phase boundary. A phase transfer catalyst is capable of taking one reactant from one phase and transferring it into another phase in which a second reactant is located and in which the first reactant, after transfer, is in a reactive form such that a reaction between the two reactants can occur. Following the reaction of the two reactants, the phase transfer catalyst is then recycled to the first phase to transfer the first reactant to the second phase in order to catalyze the reaction of another reactant molecule. Such phase transfer catalysts are described in Starks, C., Liotta, C., Halpern, M.; "Phase Transfer Catalysis" Fundamentals, Applications and Industrial Perspectives", Chapman and Hall, 1994, incorporated herein by reference.

Thus, phase transfer catalysis facilitates intimate contact of reactants that would not normally interact efficiently, usually because of phase solubility limitations. Phase transfer catalysis allows these reactions to proceed quickly, at low temperatures, and sometimes with great selectivity. A generalized example of how most PTC systems work is shown in FIG. 1 and is also known as the Starks Extraction Mechanism. In this system, the phase transfer catalyst, which may be a quaternary ammonium salt, is denoted as $Q^+Y^-$. The chemical species to be recovered is a water-soluble nucleophile, such as an anion denoted as $X^-$. The organic substrate is identified as R-Y and typically is soluble in an organic solvent and not soluble in water hence the need for a specific catalyst system to bring the reagents together. The final product is denoted as R-X. In this organic-aqueous liquid—liquid system, the positively charged catalyst cation ($Q^+$) pairs in the aqueous phase or aqueous-organic interface with the water-soluble anion or anion located at a solid surface ($X^-$), and this complex ($Q^+X^-$) reaches equilibrium across the aqueous-organic interface or solid-organic interface, as shown in FIG. 1. In this way, the positively charged catalyst cation ($Q^+$) delivers the anion to the organic phase, where it undergoes an irreversible reaction with an organic substrate (R-Y) to produce the desired product R-X.

More specifically, once formed, the ion pair ($Q^+X^-$) is a large organic species and distributes between the aqueous and organic phases. Once the phase boundary has been crossed, the reacting anion ($X^-$) reacts in an essentially irreversible reaction with a neutrally charged organic substrate affecting the desired conversion and liberating the leaving group anion, $Y^-$, which pairs with the quaternary ammonium cation to form the ion pair $Q^+Y^-$ as mentioned above and shown in FIG. 1. It should be noted that, in some phase transfer catalysis systems, the complex ($Q^+X^-$) does not move into the organic phase but undergoes the reaction with the organic substrate at the organic-aqueous interface. The ion pair, $Q^+Y^-$ comprising the quaternary ammonium catalyst and the leaving group anion, then migrates back to the aqueous phase by a reversible mechanism (either from the organic phase or the aqueous-organic interface) and can equilibrate with another target anion to regenerate $Q^+X^-$.

Many neutral and anionic nucleophiles can participate in phase transfer catalysis reactions and are also of interest to the subject invention. A long but not exhaustive list of anions includes these compounds and their derivatives: cyanide ($CN^-$), thiocyanate ($SCN^-$), cyanate ($OCN^-$), hydrogen sulfide ($HS^-$), sulfide ($S^{2-}$), carbonate ($CO_3^{2-}$), hydrogen carbonate ($HCO_3^-$), all thiocarbonates (monothio, dithio, and trithio), azide ($N_3^-$), sulfite, hydrogen sulfite, sulfate, hydrogen sulfate, thiolate ($RS^-$), nitrite, nitrate,, hydrogen selenide ($HSe^-$), selenide ($Se^{2-}$), benzenesulfonate, chloride, bromide, fluoride, iodide, trichloroacetate ($CCl_3COO^-$), thiosulfate, thiophosphorate, chlorate, hypochlorite, malonate, dichloroacetate, chloroacetate, terephtalate, adipate, lactate, silicates, bromate, periodate, performate, m-chloroperbenzoate, formate, acetate, propionate, butyrate, benzoate, furoate, oxalate, phthalate, hydrogen phtalate, phenolate, cresolate, catecholate and many more. In this context, the term "derivative" means a compound which contains one of the nucleophilic groups listed above.

Existing treatment processes of cyanide waste streams include oxidation by bleaching, electrolytic oxidation, ozonation, air oxidation, and ion exchange. Most of these processes are based on oxidation. Recently, a novel oxidation method has been described by A. Alicilar, et al. The authors indicate that 86% yield of cyanide anions removal can be achieved at 60° C. It would be desirable to develop a method which offers significantly higher yields of cyanide removal.

As an example, one system which has utilized phase transfer catalysts is the formation of alkyl or acyl cyanides (nitriles), RCN or RCOCN, from sodium cyanide, NaCN, and alkylating or acylating agents, RY, $RY_2$ and RCOY. Traditionally, aryl or alkyl cyanides have been prepared by reacting purchased or captively manufactured cyanide, $CN^-$, HCN in the form of its ionized metal salt, $CN^- M^+$, with purchased alkylating agents, RY, such as epichlorohydrin, allyl chloride, benzyl chloride, benzyl bromide, methyl chloride, and ethyl chloride, methyl bromide, ethyl bromide, methyl iodide, ethyl iodide, other alkyl halides and alkyl sulfonates such as dimethyl and diethyl sulfate, alkyl carbonates such as dimethyl or dipropyl carbonate and alkyl arenesulfates such as alkyl benzenesulfonates and tosylates, etc. Acyl cyanides can be prepared from the corresponding acyl halides (such as benzoyl chloride) and sulfonyl halides (such as p-toluenesulfonyl chloride). The technology is also usable for dihalides, $RY_2$, such as 1,4-dichlorobutane or 1,4-dichloro-2-butene.

Due to the inherent inefficiencies in many chemical processes, either HCN or NaCN, RY or $RY_2$ is either formed or allowed to become a byproduct in the event of incomplete conversion. As used herein, a non-product stream shall mean a stream which contains at least one byproduct or waste and is separate from the final product stream of a process. HCN is a volatile chemical and is either directly incinerated producing greenhouse gases and nitrous oxide pollution or scrubbed out of gas streams with caustic thus producing water soluble NaCN. Recovery of NaCN or RY may be performed by using elaborate extraction systems. Such recovery of NaCN suffers from several disadvantages, including the requirement to use an excess of inert solvent for extraction or ion exchange resin for adsorption. The expense required for extraction and recovery of $CN^-$ increases even more when the aqueous streams containing $CN^-$ are less concentrated. The expense of recovering RY may come from it being hard to distill from a compound with a close boiling point or in the case of methyl chloride or methyl bromide, the need to cryogenically compress and store these volatile gases as liquids. Similar arguments can be made for the recovery of carboxylate or phenolate anions which would take the place of cyanide in the preceding discussion.

In order to convert the recovered, purchased or manufactured HCN into RCN, it must be transformed to its salt form, $M^+CN^-$, in which $M^+$ is typically an alkali metal such as $Na^+$, $K^+$, or $Li^+$. Also, in order to convert the recovered, purchased or manufactured RY or $RY_2$ into RCN or $R(CN)_2$, it must be brought into intimate contact with the anion $CN^-$ for reaction. The conversion of HCN is typically performed by contacting concentrated aqueous solutions of metal hydroxides (e.g., NaOH, KOH, LiOH) with HCN to yield $M^+CN^-$ in concentrated solution, in solid form, or as a slurry. For example, cyano compounds=nitriles are prepared by reacting purchased HCN with benzyl chloride in the presence of aqueous sodium hydroxide and a catalyst.

Other purchased, recovered or manufactured compounds capable of forming anions which are commercially reacted with alkyl halides include carboxylic acids, cyanides, phenols, p-t-butylphenol, bisphenol A and resorcinol. Alkylating agents commercially reacted with RCOOH, NaCN, ArOH include ethyl chloroacetate and alkyl chlorides, such as methyl chloride (often formed from methanol and hydrogen chloride), ethyl chloride, and allyl chloride and alkyl bromides and iodides.

It would be desirable to develop a system which overcomes the disadvantages of purchasing, manufacturing, or recovering chemical species, such as hydrogen cyanide, HCN, carboxylic acids and their salts such as chloroacetic acid or phenol and its derivatives, ArOH, or RY or $RY_2$. In addition, it would also be desirable to develop a system which minimizes the use of an organic solvent or eliminates the need for an organic solvent altogether. Moreover, it would be desirable to utilize a system which also extracts chemical species, such as HCN from a dilute non-product stream which would have the advantages of producing a product with some value from a non-product and avoiding the need to treat the stream for that non-product. In an analogous fashion, it would also be desirable to utilize a system which could react chemical species, such as methyl chloride or allyl bromide, from a gas or liquid non-product stream which would have the advantages of producing a product with some value from a non-product and avoiding the need to treat the stream for that non-product. A process which operates continuously also would be desirable in that its automated operation would decrease the costs associated with labor and special handling of batch operations.

SUMMARY OF THE INVENTION

The present invention provides a method for making an organic product from either 1.) a chemical species dissolved in an aqueous solution at a low concentration or from 2.) a gas or liquid organic stream at low to 100% concentrations. The present invention utilizes phase transfer catalysis to transfer the water soluble chemical species from the aqueous phase to an organic phase (or to the aqueous-organic interface) which contains an electrophile, or organic substrate, and, optionally a small quantity of an organic solvent. In this way, the chemical species, which may be a contaminant in a waste stream, whether it be a water soluble anion or an organic soluble electrophile, is transferred, in the case of the water soluble anion, from an aqueous phase in which it is dilute to the organic phase or interface in which it is more concentrated, rendering it possible to undergo an efficient reaction into an organic product. If the byproduct chemical species in question is an organic soluble component in either a gas or liquid phase, it can be brought to react under phase transfer catalysis conditions with a water soluble anion that is either dilute or concentrated. The method of the present invention may be applied either on a batch or continuous basis. An example is the formation of an alkyl cyanide wherein the chemical species is sodium cyanide, and the electrophile is an alkylating agent, such as an alkyl halide.

A first embodiment of the present invention is a method for making an organic product comprising the step of contacting an aqueous solution providing an aqueous phase and having a low concentration of a chemical species comprising a nucleophile selected from the group consisting of cyanide, cyanate, carboxylate, nitrite, azide, iodide, sulfate, carbonate, and derivatives thereof with: (1) an electrophile providing an organic phase, wherein the electrophile is added in an amount to achieve an organic phase:aqueous phase ratio of 1:3 or less by weight; (2) a phase transfer catalyst for transferring the nucleophile from the aqueous phase to the organic phase or to the aqueous-organic interface to enhance a reaction in the organic phase or in the aqueous-organic interface between the nucleophile and the electrophile to form the organic product; and (3) when necessary, a pH adjusting agent in an amount sufficient to provide an excess molar concentration of base in the range between −0.99 and 1.0 molar excess.

Another embodiment of the present invention is a method for making an organic product comprising the step of contacting an aqueous solution providing an aqueous phase and having a low concentration of a chemical species comprising a nucleophile selected from the group consisting of cyanide, cyanate, carboxylate, nitrite, azide, iodide, sulfate, carbonate, and derivatives thereof with: (1) an organic solvent and an electrophile providing an organic phase, wherein said electrophile-organic component is added in an amount to achieve an organic phase:aqueous phase ratio of 1:3 or less by weight; (2) a phase transfer catalyst for transferring the nucleophile from the aqueous phase to the organic phase or to the interface to enhance a reaction in the organic phase or in the interface between the nucleophile and the electrophile to form the organic product; and (3) when necessary, a pH adjusting agent in an amount sufficient to provide an excess molar concentration of base in the range between −0.99 and 1.0 molar excess.

The embodiments discussed above and the others described herein can also be used when the nucleophile is phenolate or derivatives thereof. In this event, the electrophile and optional organic solvent are added in an amount to achieve an organic phase:aqueous phase ratio of 1:6 or less by weight.

Another embodiment of the present invention is a method for making an organic product comprising the step of contacting an aqueous solution providing an aqueous phase and having up to ten weight percent of a chemical species of interest which comprises a target anion or is capable of being ionized to produce the target anion with a phase transfer catalyst, an organic phase consisting of an electrophile, and a pH adjusting agent in an amount sufficient to provide an excess molar concentration of base in the range between −0.99 and 1.0. The phase transfer catalyst functions to transfer the target anion from the aqueous phase to the organic phase or interface, thereby enhancing a reaction in the organic phase or the interface between the target anion and the electrophile to form the organic product. In the event that the chemical species is not in the form of a target anion but instead is only capable of being ionized to produce the target anion (i.e., it exists as a non-dissociated neutral compound), the method also includes adding the pH adjusting agent, either to the aqueous solution or to the mixture of the aqueous solution, the organic phase, and the phase transfer catalyst, in an amount sufficient to raise the pH in the aqueous phase to a level sufficient to ionize the chemical species.

Another embodiment of the present invention is a method for continuously converting a chemical species in an aqueous waste or byproduct stream to a product. This method involves the steps of contacting the aqueous non-product stream, which has a low concentration of the chemical species, with a phase transfer catalyst, an organic solvent, an electrophile providing an organic phase, and a pH adjusting agent in an amount sufficient to provide an excess molar concentration of base in the range between −0.99 and 1.0. Alternatively, no solvent may be included, such that the organic phase consists of an electrophile or an organic substrate. The phase transfer catalyst serves to transfer the nucleophile, such as a target anion, from the aqueous phase to the organic phase or interface and thereby enhances a reaction in the organic phase or interface between the nucleophile and the electrophile to form the organic product. Subsequently, the aqueous phase is separated from the organic phase. If the phase transfer catalyst is in the organic phase, it is divided into the product and the phase transfer catalyst, which may be recycled. In some cases, the phase transfer catalyst is water soluble and can be recovered from or left in the aqueous phase.

Yet another embodiment of the present invention is a method for improving the quality or increasing the purity of an aqueous non-product stream having a contaminant comprising a nucleophile. This method involves first contacting the aqueous non-product stream with an electrophile and optionally an organic solvent (providing an organic phase), a phase transfer catalyst for transferring the nucleophile from the aqueous phase to the organic phase or the interface to enhance a reaction in the organic phase-or in the interface between the nucleophile and the electrophile to form the organic product, and when necessary, a pH adjusting agent in an amount sufficient to provide an excess molar concentration of base in the range between −0.99 and 1.0. Then, the aqueous phase is separated from the organic phase, to provide an aqueous stream having a reduced concentration of the contaminant.

Another embodiment of the present invention is the method for making an organic product from byproducts comprising the step of contacting a non-product stream consisting of an organic solution providing an organic phase, either as a gas or liquid, and having a chemical species comprising an electrophile with: (1) water providing an aqueous phase and a nucleophile in concentrations of 0.001 wt % to the saturation limit of the nucleophile in water and preferably between 1 and 50 wt %, more preferably between 5 and 20 wt %, wherein water may be added in an amount to achieve an organic phase:aqueous phase ratio of 1:3 or less by weight; (2) a phase transfer catalyst for transferring the nucleophile from the aqueous phase to the organic phase or interface to enhance a reaction in the organic phase or interface between the nucleophile and the electrophile to form the organic product; and (3) when necessary, a pH adjusting agent in an amount sufficient to provide an excess molar concentration of base in the range between −0.99 and 1.0 molar excess.

Another embodiment of the present invention is a method for continuously converting a chemical species in an organic waste or byproduct stream to a product. This method involves the steps of contacting the organic non-product stream, which can have a concentration of 0.001 to 100 wt % of the chemical species, with a phase transfer catalyst, an organic solvent, water containing a nucleophile in concentrations between 0.001 to the saturation limit of the nucleophile in water, and, if necessary, a pH adjusting agent in an amount sufficient to provide an excess molar concentration of base in the range between −0.99 and 1.0 molar excess. Alternatively, no solvent may be included, such that the organic phase consists of an electrophile or an organic substrate. The phase transfer catalyst serves to transfer the nucleophile, such as a target anion, from the aqueous phase to the organic phase or interface and thereby enhances a reaction in the organic phase or interface between the nucleophile and the electrophile to form the organic product. Subsequently, the aqueous phase is separated from the organic phase. If the phase transfer catalyst is soluble in the organic phase then the organic phase is divided into the product and the phase transfer catalyst, which may be recycled. In some cases, the phase transfer catalyst is water soluble and can be recovered from or left in the aqueous phase.

Yet another embodiment of the present invention is directed to a method for improving the quality or increasing the purity of an organic non-product stream having a contaminant comprising an electrophile. This method involves first contacting the organic non-product stream with water containing a nucleophile in concentrations between 0.001 wt % to the saturation limit of the nucleophile in water, and preferably between 1 and 50 wt %, more preferably between 5 and 20 wt %, and, when necessary, a pH adjusting agent in an amount sufficient to provide an excess molar concentration of base in the range between −0.99 and 1.0, and a phase transfer catalyst for transferring the nucleophile from the aqueous phase to the organic phase or interface to enhance a reaction in the organic phase or in the interface between the nucleophile and the electrophile to form the organic product. Then, the aqueous phase is separated from the organic phase, to provide an organic stream having a reduced concentration of the contaminant.

It is to be understood that both the foregoing general description and the following detailed description are exemplary, but are not restrictive, of the invention.

BRIEF DESCRIPTION OF THE DRAWING

The invention is best understood when read in view of the attached drawing, in which.

DETAILED DESCRIPTION OF THE INVENTION

Figure 1:
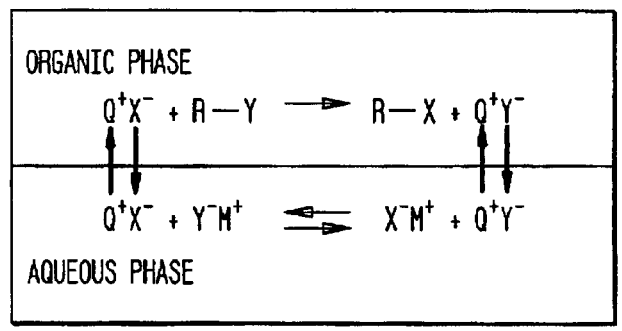
FIG. 1 shows one mechanism of a phase transfer catalysis system.

The present invention is directed to a method for making an organic product using phase transfer catalysis. As described above, one chemical mechanism for phase transfer catalysis is shown in FIG. 1. Another mechanism mentioned above involves a reaction at the aqueous-organic interface instead of in the organic phase. The methods of the present invention are not limited to any one specific mechanism of phase transfer catalysis. In particular, different constituents may undergo different mechanisms and one system might undergo more than one mechanism, including the two discussed herein or some other known mechanism for phase transfer catalysis.

According to the present invention, the chemical species is contacted with a phase transfer catalyst, when necessary a pH adjusting agent in an amount sufficient to provide an excess molar concentration of base in the range between −0.99 and 1.0, preferably between −0.25 and 0.5, more preferably between stoichiometric and 0.25, and most preferably between 0.01 and 0.1. As used herein, the term "stoichiometric" means the amount of base (or base, such as sodium hydroxide) which would be needed to completely react with the compound to form a complex consisting of a cation-anion pair derived from the base and the target anion. Thus, the "excess molar concentration of base" is the amount of base actually in the system above that which would be stoichiometrically required to neutralize ionizable hydrogen atoms and is expressed herein as the difference between the actual concentration of base and the stoichiometric concentration divided by the stoichiometric concentration. Thus, a negative value of excess molar concentration of base contemplates that less than complete conversion into anion is desired. The greatest excess molar concentration of base according to the present invention is only about 1.0, with the maximum in a preferred embodiment being only 0.5 and in the most preferred embodiment being only 0.1. This is a relatively small amount of excess base, especially when compared to certain prior art teachings. Moreover, certain references teach that yield is decreased with decreasing amounts of base and encourage much greater excess of base.

According to an embodiment of the invention, when the chemical species (i.e., the constituent being removed from a by-product or waste stream) serving as a reactant exists as a nucleophile, it is contacted with an organic phase consisting solely of an electrophile along with the phase transfer catalyst. On the other hand, when the chemical species must be ionized to function as a nucleophile, the amount of the pH adjusting agent is selected to ensure that the pH is raised to a level sufficient to ionize the chemical species, namely by removing a proton from the species and generating a negatively charged species. Such a pH is dependent on the nature of the nucleophile, namely whether it exists as a strong or weak acid. Thus, when the chemical species already exists as a target anion or as a neutral compound that can act as a nucleophile, no pH adjusting agent is needed. When a pH adjusting agent is needed, the particular amount of the agent or base will vary depending on process conditions, but can be optimized easily by altering the concentration and determining its effect on yield, bearing in mind the ranges of excess molar concentrations set forth above. This preferred embodiment in which no pH adjusting agent is required is particularly applicable to treating waste or by-product aqueous streams (collectively "non-product streams") having a target anion (such as carboxylate, RCOO⁻, cyanide, CN⁻, or phenolate, ArO⁻) at the existing pH of the non-product stream or a neutral compound which can act as a nucleophile (such as hydrogen peroxide or amines), as opposed to an aqueous stream having a chemical species which must be ionized before it can react with the catalyst. In many non-product streams, the pH of the streams is already sufficiently high to ionize the chemical species.

An embodiment of the present invention recognizes that phase transfer catalysis can be carried out in the absence of an organic solvent (i.e., the organic phase consists of an electrophile) or with not much solvent (i.e., the organic:aqueous phase ratio is 1:3 by or less by weight) and for the purposes of either removing a chemical species from a low concentration or dilute aqueous stream or removing a chemical species from a gas or liquid organic stream.

Figure 2:
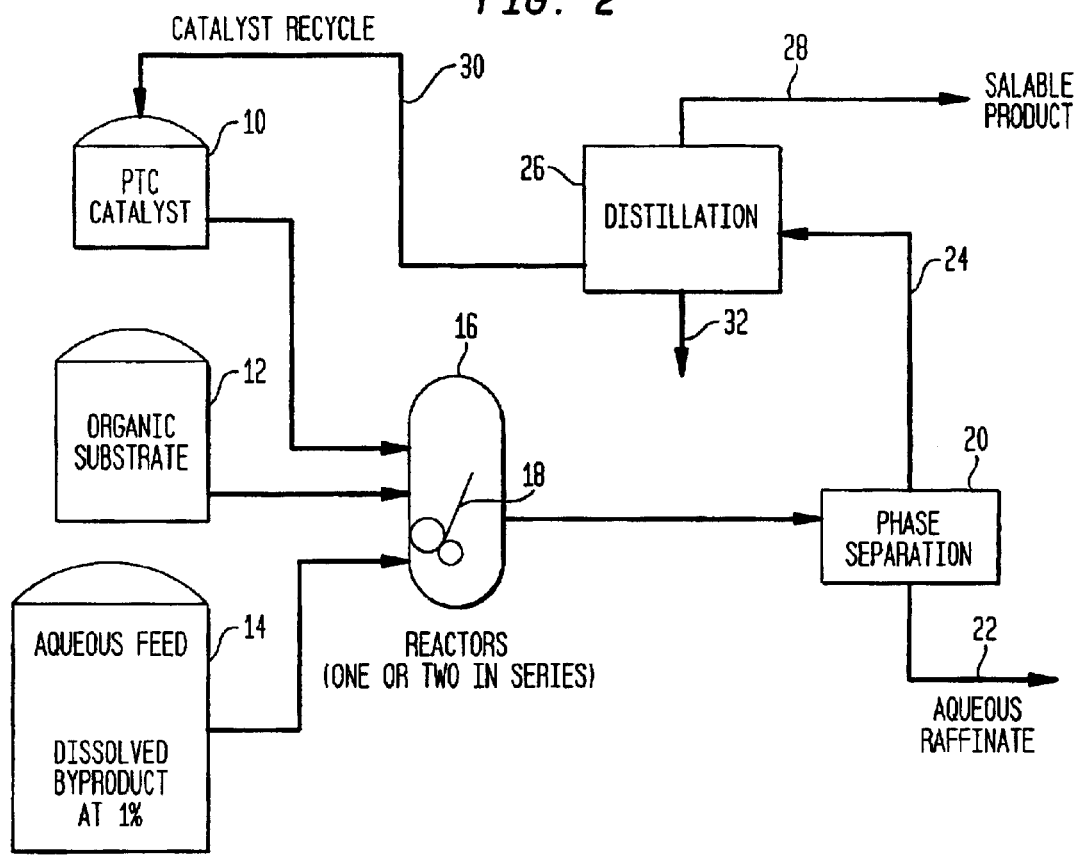
FIG. 2 is a schematic diagram of a system used to continuously convert a chemical species in an aqueous waste stream to an organic product.

The contacting step can be carried out in any suitable reactor, either batch or continuous, the latter of which is described below in connection with FIG. 2. The chemical species is initially present in the aqueous phase, such as in an aqueous waste or by-product stream, and is used to make the organic product can be any of a wide range of possible species. Such chemical species are generally described as nucleophiles, which are defined as an anion or molecule having a high electron density which is accessible for reaction with another molecule bearing a low electron density which is accessible for reaction. Most nucleophiles of interest are anions and are referred to herein as "target anions." For example, suitable compounds which contain target anions or are capable of being ionized to produce the target anion and which may be present in low concentration or dilute aqueous solutions, include cyanide salts, nitric acids and their salts, carboxylic acids and their salts, e.g. carboxylates, sodium acetate, potassium benzoate, propionic acid, acrylic acid, benzoic acid, salicylic acid and the like, phenol and substituted phenols (such as phenol, cresols, xylenols, t-butyl phenol, hydroquinone, catechol, resorcinol, bisphenol A, bisphenol S, bisphenol F, other bisphenols, brominated bisphenols, bromoxynil, chlorophenol, polychlorophenols, phenolic steroids, their salts and the like) heterocycles bearing an N—H group (such as pyrrole, imidazole, carbazole, indole, purines, pyrimidines and the like), mercaptans and their salts (such as methyl mercaptan, thiophenol and the like), and other anionic nucleophiles (such as cyanate, thiocyanate, azide, iodide, and the like). The invention may be used when the target anion is cyanide also known as CN⁻ or carboxylate, RCOO⁻ where R is an alkyl or aryl group, or phenolate, ArO⁻. It should be noted that nucleophiles which are not anions may be used in the present invention. Such compounds include, for example, primary, secondary amines such as mono alkyl and dialkyl amines. The relevant product of reactions using these nucleophiles are amines, ammonium salts, amides, amidinium salts, sulfonamides and the like.

Similarly, the chemical species which is initially present in the organic phase, such as in an organic waste or by-product stream, can be any of the "electrophiles" or "organic substrates" as discussed below. For example, the process of the present invention could be used to react an alkyl halide, such as methyl bromide, from an organic waste or byproduct stream and convert it into a less harmful chemical. The use of the present invention in this way may have particular utility in that methyl bromide is known to be a fumigant or spore destroyer but, when released to the atmosphere, it causes ozone depletion. Thus, one embodiment would be to contact methyl bromide which had been used as a fumigant with an aqueous stream containing a nucleophile, such as sodium nitrite, a phase transfer catalyst, and a pH adjusting agent, to form nitromethane and sodium bromide, which are more environmentally friendly than methyl bromide. Alternative and faster reacting anions can be thiosulphate or sulphite. These may be used to destroy the hazardous component (electrophile) without making a salable product. Thus, the present invention is also applicable to hazardous waste abatement.

If the chemical species exists in the form of a neutral compound, and has to be transformed into a target anion to serve as a nucleophile, the amount of the pH adjusting agent selected must take into account that the pH must be sufficient to cause the chemical species to ionize, bearing in mind that the amount of pH adjusting agent should fit within the ranges set forth above, namely that the excess molar concentration of base fall within −0.99 and 1.0. The pH sufficient to cause ionization varies over a wide range depending on a number of factors, such as the specific chemical species used and the particular pH adjusting agent used. Once ionized, a proton has been removed from the chemical species and has generated a negatively charged species X⁻, namely the target anion. A suitable pH includes ranges at which the target anion is present and is at least partially soluble in the aqueous solution, which is generally above pH of 3, preferably pH 9 to 13.5 for phenol and substituted phenols. As shown in one of the examples below, however, the present invention may work even at lower pH values, including a pH of 1. It should be recognized that the pH as used herein refers to the pH in aqueous phase. The pH adjusting agent could be added first to the aqueous solution or could be added after the aqueous phase has been mixed with either or both of a phase transfer catalyst and an organic phase consisting of an electrophile. Any number of suitable pH adjusting agents could be used, but some typical ones are sodium hydroxide, potassium hydroxide, magnesium hydroxide, calcium hydroxide, lithium hydroxide, ammonium hydroxide, magnesium carbonate, calcium carbonate, tetralkyl ammonium hydroxides, sodium and potassium carbonates, hydrogen carbonates, phosphates, similar salts, and mixtures thereof. For many anions, no pH adjustment is needed. For example, salts when dissolved in water are fully dissociated and have their anion available for reaction. Also, strong acids, such as trichloroacetic acid, are ionized even at a very low pH of 1.

As mentioned above, it has been found particularly desirable to employ the methods of the present invention when the chemical species is present in a low concentration in the aqueous phase, such as less than 25 weight percent. More preferably, the method described herein is suitable for use when the chemical species is in a dilute amount, up to 15 weight percent in the aqueous phase, more preferably up to 10 weight percent, still more preferably between 0.001 and 5 weight percent, and most preferably between 0.001 and 1 weight percent. Some industrial waste or by-product streams contain about 6 weight percent chemical species; therefore a preferred range might be between about 5 and 7 weight percent for such systems. Thus, although it would be difficult to cause the chemical species to undergo a reaction in the aqueous phase at such low concentrations, such reactions are not so difficult after the nucleophile, such as the target anion, is transferred from the aqueous phase to the aqueous-organic interface or to the organic phase where it is one of only two constituents, both of which are reactants, namely the target anion (X⁻) and the organic substrate (R-Y), as shown in FIG. 1.

Turning to the organic substrate, the term "electrophile" as used herein is also given its common meaning, namely a molecule or ion which bears a low electron density which is accessible for reaction. As mentioned above, the organic substrate of the present invention may be an alkylating agent or acylating agent, which may be an alkyl halide, an acyl halide, a sulfonyl halide, an anhydride or other electrophilic agent capable of liberating a leaving group when reacted with a nucleophile. Suitable alkylating agents include compounds in which leaving groups are bonded to a primary or secondary aliphatic carbon. Suitable leaving groups include chloride, bromide, iodide, benzenesulfonate, toluenesulfonate, methanesulfonate and the like. Suitable alkylating agents also include epichlorohydrin, allyl chloride, allyl bromide, benzyl chloride, benzyl bromide, methyl chloride, dimethyl carbonate, methyl p-toluenesulfonate, dimethyl sulfate, ethyl chloride, ethyl bromide, diethyl sulfate, n- and iso-propyl chloride, n- and iso-propyl bromide, and all other alkylating agents of the formula $C_nH_wX_yO_z$ where C is a carbon atom, H is a hydrogen atom, O is an oxygen atom, X is one of the group Chloro, Bromo, Iodo or $ArSO_3$ where Ar is an aryl group, S is sulfur and O is oxygen and n can take on all values of 1 to 20, wherein the sum of w, y and z cannot exceed (2n+2), preferably y is equal to 1 or 2, more preferably y is equal to 1 and z can take on values of 0 to 3. A suitable acylating agent is benzoyl chloride, benzenesulfonyl chloride or p-toluene sulfonyl chloride. Preferred alkyl halides include alkyl chlorides such as benzyl and methyl chloride, alkyl bromides such as allyl and benzyl bromide, and epichlorohydrin. In addition, preferred acyl halides include benzoyl chloride and stearoyl chloride. In selecting a compound to serve as an organic species, it is preferable to select a compound which does not quickly degrade in water.

The phase transfer catalyst for transferring the target nucleophile from the aqueous phase to the organic phase or interface to enhance a reaction in the organic phase or interface between the target anion and the electrophile to form the organic product can be any suitable phase transfer catalyst. As used herein, the term "enhance" in this context shall mean increasing the rate or extent of a reaction which would have occurred even in the absence of the phase transfer catalyst and enabling a reaction to occur which would not have occurred at all in the absence of the phase transfer catalyst. both Suitable phase transfer catalysts include quaternary ammonium salts, quaternary phosphonium salts, quaternary arsonium salts, polyethylene glycols, ethers of polyethylene glycols, crown ethers, cryptands, tertiary amines, polymer bound phase transfer catalysts, phase transfer catalysts adsorbed on supports such as silica and clay and the like. Suitable phase transfer catalysts also include tricaprylylmethylammonium chloride, tetrabutylammonium bromide, tetrabutyl ammonium hydrogen sulfate, methyltributylammonium chloride, benzyl triethyl ammonium chloride, triethylamine, tributylamine, trioctylamine, tetrabutylphosphonium bromide, tetraphenylphosphonium bromide, 18-crown-6, dibenzo-18-crown-6, benzo-15-crown-5, polyethylene glycol with a molecular weight in the range of 300 to 3000, the dimethyl and dibutyl ethers of said polyethylene glycols, Tris(3,6-dioxaheptyl)amine (also known as TDA-1) and the like. Preferably, the phase transfer catalyst is selected from the group consisting of a quaternary ammonium salt, a quaternary phosphonium salt, a crown ether, cryptand and polyethylene glycol. More preferably, the phase transfer catalyst is a quaternary ammonium salt selected from the group consisting of methyltricaprylylammonium chloride and tetrabutylammonium bromide. Most preferably, the phase transfer catalyst is tricaprylylmethylammonium chloride, which is commercially available under the trademark Aliquat 336 or Aliquat 128 or Adogen 464.

Although the present invention is discussed primarily from the viewpoint that the chemical species is from a waste or byproduct aqueous phase, the same considerations and approaches are used when the chemical species is from a waste or byproduct organic phase. For example, if an industrial process is producing an organic waste or byproduct stream containing an alkyl halide, one could form an alkyl cyanide by contacting that stream with a phase transfer catalyst, and an aqueous phase having cyanide, in the same way that an alkyl halide (either with or without a solvent) can be contacted with an aqueous waste or by product stream containing cyanide to make an alkyl cyanide. In sum, the present invention contemplates methods for making an organic product from either a byproduct or waste aqueous stream or a byproduct or waste organic stream. The concentration of the electrophile in an organic stream can vary over a wide range, such as between about 1 to 100 wt %, but is preferably on the high end, such as between about 50 to 100 wt % and most preferably between about 80 to 100 wt %. This embodiment is particularly desirable when the method of the present invention is used to treat an organic non-product stream which has a contaminant which is an electrophile.

One embodiment of the present invention takes advantage of non-product aqueous streams that contain specific anions. In this embodiment, it is only necessary that the pH value be sufficiently high such that the chemical species is completely (or substantially completely) dissociated to ions and the deriving anion is available for reactions. The extent of dissociation depends on the needs of the particular application, but most often a dissociation of at least 90% is acceptable, although some applications might dictate a dissociation of at least 99% or even 99.9%. For anions deriving from strong acids such as p-toluenesulfonic or trichloroacetic acids, the pH of the used aqueous phase can be either acidic or basic. Even at low pH values, strong acids are almost completely dissociated to ions and the deriving anion is available for reactions. At high pH values, the corresponding salt such as sodium p-toluene sulfonate or trichloroacetate is also completely dissociated and the anion can be transported into the organic phase and react. In the case of weak acids such as acetic acid or 1-naphthol, the deriving anions are available for the reaction only at higher pH values when the corresponding salt (for example, sodium acetate or potassium 1-naphthoate) is completely ionized. For example, acetic acid is over 90% ionized at pH of 6. At the lower pH, the acid is present mostly in the non-ionized form. While it may be still reactive, it is advantageous to increase the pH to transform the acid into the corresponding anion which is almost always a better nucleophile. Most aqueous streams containing anions which can be removed according to the present invention exhibit a sufficiently high pH, such as a basic pH, such that the chemical species is substantially completely ionized. Such streams do not require any pH adjustment.

One of the aspects of the present invention is the formation of materials of commerce as a result of above mentioned phase transfer catalysis enhanced processes. Thus, starting from non-product aqueous streams containing low concentrations of anions of interest and reacting these anions with appropriate electrophiles such as alkylating or acylating agents, one can produce salable products. Subsequently, these products must be isolated from the aqueous phase and purified by such separation methods as distillation, chromatography, crystallization, and extraction.

Another embodiment of this invention is the use of phase transfer catalysts to enhance reactions between electrophiles forming the organic phase and anions present in low concentration or diluted aqueous streams to remove these anions from industrial aqueous streams. For example, cyanide waste streams are produced by several industries including ore extraction, photographic processing, manufacturing of synthetic organic and inorganic compounds and metal finishing. Aqueous solutions containing various form of cyanides are of major environmental concern. The methods described herein may be used to treat such a stream and form a salable or non-salable product. In the latter case, the invention can be characterized as a method for purifying an aqueous non-product stream. Similarly, if an organic non-product stream is being treated to remove an electrophile which is a contaminant to form a non-salable product, then the invention can be characterized as a method for purifying an organic non-product stream. (As used herein, the term "product" does not necessarily mean a salable or value-added product, but is merely referring to a product of a chemical reaction.)

Another category of compounds that can be similarly treated are carboxylic acids and their salts. When reacted with appropriate alkylating agents, salts of carboxylic acids produce carboxylate esters. Such esters are usually formed as a result of reaction between acids and alcohols often in a presence of appropriate catalyst such as a mineral acid or dicyclohexylcarbodiimide (DCC) and 4-dimethylaminopyridine. Phase transfer catalysis mediated reactions of carboxylic salts with alkylating agents have been exploited as well. The present invention relates to the formation of the above mentioned esters from carboxylic and similar acids and their salts present at industrial and other waste waters at low concentrations. The produced esters are usually insoluble in water, and thus, can be easily separated.

It is often advantageous to include a co-catalyst in the reaction. Such a co-catalyst serves to enhance the reaction rate in the organic phase (i.e., the top reaction shown in FIG. 1). Typical co-catalysts may include sodium iodide, potassium iodide, and other alkaline earth metal iodide species. They are preferably mixed in with the aqueous phase, either before mixing with the organic phase or afterwards. The operating conditions of the contacting step should be selected to optimize the reaction in the organic phase, as shown in FIG. 1. As that reaction proceeds more quickly, then the entire scheme is caused to move more efficiently as dictated by Le Chatelier's Law. More specifically, as the catalyst cation/target anion ($Q^+X^-$) ion pair reacts in the organic phase, the ion pair previously existing in the aqueous phase is driven to the organic phase.

The preferred conditions depend on a number of factors, including the specific chemical species used, the organic substrate used, and the phase transfer catalyst used. In general, the time, temperature and agitation should be selected to cause the reaction in the organic phase to proceed efficiently. Suitable temperatures in some scenarios include temperatures at which the reaction proceeds, typically 10° C. to 200° C., preferably 10–80° C., and most preferably 30–70° C. As is well-known, the choice of temperature is dictated by the kinetics of the reaction. Reactions which occur more slowly are preferably run at higher temperatures. In addition, some reactions, such as the formation of benzoyl cyanide from benzoyl chloride and cyanide, occur so quickly that it is desirable to run such reactions at low temperature, for example in an ice bath. Suitable molar ratios of alkylating agent to nucleophile are 0.5:1 to 1000:1, preferably 0.5:1 to 10:1, more preferably 0.5:1 to 1:5. Another type of co-catalyst may affect a selectivity of reaction with ambient anions. For example, when benzyl chloride is reacted with thiocyanate anion, benzyl thiocyanate is the only product (no benzyl isothiocyanate) when the reaction is performed in the presence of catalytic amounts of copper(1) thiocyanate.

According to another embodiment of the present invention, a chemical species of an aqueous non-product stream is continuously converted to a product. As shown in FIG. 2, a phase transfer catalyst from its feed tank 10, an organic substrate from its feed tank 12, and an aqueous feed from its feed tank 14 are all fed to a reactor 16 where the three are contacted with one another. Aqueous feed tank 14 contains the chemical species which is present at a low or dilute concentration. Although not shown, a pH adjusting agent may also have its own feed tank and may be directed to reactor 16 or to aqueous feed tank 14. In the event a solvent is used, it may be contained in feed tank 12, where the organic substrate is. Also, the catalyst may be dissolved in feed tank 12 thus lowering installation costs.

After the constituents (and optional solvent) are contacted with one another for an adequate contact time across reactor 16, where they may be mixed by mixing element 18 or by a normal impeller-mixer, the stream exiting reactor 16 is directed to phase separator 20, which may be a liquid— liquid centrifugal separator, for example. From separator 20, aqueous raffinate stream 22 and organic phase stream 24 result. Aqueous raffinate stream 22 is typically discarded or further treated, as needed, to remove residual water-soluble organic components that were part of the original feed or were unreacted. Organic phase stream 24 is directed to a distillation column 26, where the organic phase is divided into at least the product in product stream 28 and the catalyst in catalyst stream 30. Another organic byproduct stream 32 (which includes catalyst degradation products) is shown in FIG. 2, although this stream might not be present if there is a high level of purity or if there is some impurity but it is acceptable to mix this impurity in with the catalyst in catalyst stream 30. Catalyst stream 30 is recycled by being directed to catalyst feed tank 10. As an alternative to using a distillation column, a membrane filter may be used. In this event, the permeate stream is the product and the retentate stream includes the catalyst and any catalyst degradation products with a molecular weight higher than the cut-off weight for the membrane. In some instances, recycling the alkyl halide can be done via a one stage flash equilibrium separation.

The various embodiments of the present invention discussed above in connection with a batch process similarly apply to a continuous process. For example, a continuous process according to the present invention can be run with or without a solvent or with or without a pH adjusting agent. Moreover, the particular constituents and products formed are not critical for carrying out the purposes of the present invention in either a batch or continuous process.

The present invention is suitable for the preparation of an alkyl cyanide from hydrogen cyanide or sodium cyanide, NaCN (which is made by contacting HCN with sodium hydroxide, NaOH) which is dissolved in a byproduct or waste stream. Typically, the pH of the byproduct or waste stream is 8 or higher, and the sodium cyanide is at a concentration of 10 or 5 weight percent or less. An advantage of the present invention is that a nucleophile such as cyanide or phenol need not be purchased, recovered, or manufactured. Cost savings are further achieved in the present invention by avoiding the waste treatment cost associated with treating the byproduct or waste stream containing NaCN. Often, waste streams containing NaCN are classified as hazardous waste. Thus, the cost savings associated with minimizing treatment of hazardous waste in the present invention may be significant. Another advantage of the present invention is that pollution prevention is achieved by reducing the quantity of waste NaCN and converting it into a value added product, RCN. Another advantage of the embodiments of the present invention in which no solvent is used, emissions and other environmental issues associated with a solvent are eliminated or significantly reduced.

In addition to the formation of an alkyl cyanide from hydrogen cyanide, specific systems that the method is applicable to are: formation or production of an aryl alkyl ether from phenol or a substituted phenol; benzyl cyanide from benzyl chloride and sodium cyanide; benzyl cyanide from benzyl bromide and potassium cyanide; benzyl cyanide from benzyl bromide and lithium cyanide; benzyl acetate from benzyl chloride and sodium acetate; and benzyl benzoate from benzyl chloride and sodium or potassium or lithium benzoate A preferred phase transfer catalyst being the quaternary ammonium salt sold under the trademark Aliquat 336 or Adogen 464.

There are many other possible systems, with a constraint being that an organic substrate or product which hydrolyzes readily in an aqueous environment may tend to limit the yield of the reaction. In such cases, it may be desirable to include a solvent in the system to help minimize the decomposition of the organic substrate, for example up to the 1:3 organic phase:aqueous phase weight ratio or to run at a reduced temperature. In the event that a solvent is used, such solvents include benzene, toluene, methyl isobutyl ketone, dichloro methane, dichloroethane, chlorobenzene, dichlorobenzene, xylene, kerosene, alkanes, esters and ethers and the like which are immiscible with water but in which the electrophile can be used with minimal decomposition and side reactions, may also be used. The above are typical examples and do not represent a comprehensive list.

One particular application of the invention could be to the effluent end of a fermentation plant, in which the invention could be used to recover products from dilute aqueous streams and convert them at low concentrations into salable products. For example, lactic acid is made from many fermentation processes, and this could be used to form ethyl lactate by combining the aqueous effluent stream containing lactic acid with ethyl chloride.

It has been found that it is desirable to run solvent-free reactions in many cases because the reaction rate in the organic phase (i.e., the top reaction shown in FIG. 1) is significantly enhanced due to the increased concentration of the electrophile in the organic phase. On the other hand, a solvent is preferable when it is necessary to slow a reaction down that otherwise goes too fast which could result in unnecessary heat effects, among other disadvantages. Preferably, the organic phase:aqueous phase weight ratio is 1:3 or less (preferably 1:6 or less) if the nucleophile is cyanide, cyanate, carboxylate, sulfonate carbonate, nitrite, azide, iodide, and derivatives thereof. If the nucleophile is phenolate, the organic phase:aqueous phase weight ratio should be 1:6 or less. Regardless of the nucleophile, the organic phase:aqueous phase weight ratio may preferably be 1:10 or less and still more preferably 1:20 or less. Moreover, it is usually advantageous when the organic substrate is in liquid form at the operating conditions for the reactions to occur. If the organic substrate is a solid, then it is usually beneficial for it to be dissolved in a suitable organic solvent.

EXAMPLES

The chemicals were purchased from the vendors as listed below and used as purchased without any additional purification. Tap water was used to prepare the aqueous phase. All the chromato-graphic analyses were performed using a Hewlett-Packard/Agilent 6890 Gas Chromatograph with an HP/Agilent 6890 Series Integrator and a TCD detector with EPC and J&W Scientific DB-Wax column. The column conditions were: oven 95° C., initial time—1 minute, rate—15° C./min, final temp.—225, final time—3 minutes, total run time 12.66 minutes. The inert gas was ultra pure helium from AirGas. For most reactions, solutions containing four different reactants concentrations were prepared to determine the response factors of the reactants against the gas chromatographic internal standard. If no solvent was used in the reaction, the organic reactant was used as a solvent in these measurements. In the examples below, the reaction conditions were not exhaustively tested to optimize the conversion, and most of the samples were taken while the reaction was still progressing.

Example 1

Benzyl Cyanide (Phenylacetonitrile)

A mixture consisting of sodium cyanide (2.94 g, 60 millimoles, Aldrich, 95+%), sodium iodide (0.93 g, 6 millimoles, Aldrich, 98%), sodium hydroxide (0.12 g, 3 millimoles, Merck, 97%, to neutralize any possible hydrogen chloride formed from hydrolysis of benzyl chloride), and water (300.63 g) was introduced to a three-necked 500 mL flask and warmed to 40° C. This aqueous solution was treated with a mixture consisting of benzyl chloride (30.38 g, 240 millimoles, Aldrich, 97%), Aliquat 336 (2.58 g, 6 millimoles, Aldrich), and durene (GC standard, 1.34 g, 10 millimoles, Aldrich, 98%), and next, the two phase system was continuously stirred at 600 rpm (the rate of stirring was temporarily checked with a calibrated photo-tachometer from VWR). The organic phase:aqueous phase weight ratio was 1:9. The reaction mixture was kept at constant temperature of 40° C. After 60 minutes of reaction, an aliquot was taken, briefly centrifuged and the phases were separated. The organic phase of the aliquot was injected into the gas chromatograph. The yield of benzyl cyanide based on the limiting reactant (sodium cyanide) was 92%. A small amount of benzyl iodide (about 2%) was present in the reaction mixture. Analysis performed on the aqueous phase showed that the concentration of the cyanide anion, was decreased from 10000 ppm to 0.75 ppm.

Example 2

Benzyl Thiocyanate

A mixture consisting of sodium thiocyanate (1.53 g, 19 millimoles, Aldrich, 98%), sodium iodide (0.15 g, 1 millimole, Aldrich, 98%), copper (I) thiocyanate (0.142 g 1.1 mmoles, Aldrich, 99%), and water (179.25 g) was introduced to a three-necked 500 mL flask and warmed to 40° C. This mixture was then treated with benzyl chloride (7.59 g. 60 millimoles, Aldrich, 97%), benzyl acetate (GC standard, 0.75 g, 5 millimoles, Aldrich, 99+%), and Aliquat 336 (0.86 g, 2.0 millimoles, Aldrich). The organic phase:aqueous phase weight ratio was 1:20. The two phase system was continuously stirred at 600 rpm (the rate of stirring was temporarily checked with a calibrated photo-tachometer from VWR) while the reaction mixture was kept at constant temperature of 40° C. After 180 minutes of stirring, the aliquot was taken, briefly centrifuged and the organic phase was injected into the gas chromatograph. The yield of benzyl thiocyanate based on the limiting reactant (sodium thiocyanate) was 63%. Additionally, the reaction mixture contained a small amount (below 1%) of benzyl iodide.

When the reaction was performed without copper (I) thiocyanate, the major product (benzyl thiocyanate) was accompanied by about 15% of an additional product—most likely benzyl isothiocyanate. In the presence of copper (I) thiocyanate, the only product was benzyl thiocyanate.

Example 3

Benzyl Benzoate

A mixture comprising benzoic acid (2.45 g, 20 millimoles, Aldrich, 99%), sodium hydroxide (1.90 g, 22.5 millimoles, 50% w/w solution in water, Aldrich) and water (247.2 g) was stirred magnetically at room temperature for about two hours until the solids dissolved in water. The excess molar concentration of sodium hydroxide was 0.125. Next, the aqueous phase was transferred to a three-necked 500 mL flask and warmed up to 45° C. The organic phase consisting of benzyl chloride (7.60 g, 60 millimoles, Aldrich, 97%), 3-methylanisole (GC standard, 0.616 g, 5 millimoles, Aldrich, 99%), and Adogen 464 (0.905 g, 2 millimoles, Aldrich) was added to the aqueous phase and the two phase system was stirred mechanically (600 rpm, a calibrated photo-tachometer) for three hours at 45° C. The organic phase:aqueous phase weight ratio was 1:27. The aliquot, taken after 180 minutes after the addition of the organic phase, was briefly centrifuged, the phases were separated and the organic phase was injected into the GC instrument. The yield of benzyl benzoate based on the limiting reactant (benzoic acid) was 87%. Benzyl Benzoate was accompanied by a small quantity of benzyl alcohol (less than 5%).

Example 4

Benzyl Benzoate in the Presence of Sodium 4-Hydroxybenzoate

A mixture consisting of benzoic acid (2.44 g, 20 millimoles, Aldrich, 99%), sodium 4-hydroxybenzoate (3.21 g, 20 millimoles, Aldrich, 99%), sodium hydroxide (1.72 g of 50% w/w solution, 21 millimoles, Aldrich), sodium iodide (0.12 g, 0.80 millimoles, Aldrich, 98%), and water (281.20 g) was stirred magnetically overnight in the three-necked 500 mL flask to produce a single phase. The mixture was warmed up to 45° C. and treated with the organic phase comprising of benzyl chloride (10.13 g, 80 millimoles, Aldrich, 97%), 3-methylanisole (GC standard, 1.89 g, 15 millimoles, Aldrich, 99%), and Adogen 464 (0.81 g, 2.0 millimoles, Aldrich). The organic phase:aqueous phase weight ratio was 1:22. The reaction mixture was kept at 45° C. and stirred mechanically at the rate of 600 rpm (measured with a calibrated photo-tachometer). The aliquots were taken from the reaction mixture at 0, 30, 60, 120, 180 minutes after the addition of the organic phase. The aliquots were briefly centrifuged and the organic phase was injected into the GC instrument. After 180 minutes of reaction practically the only product formed was benzyl benzoate (54% yield based on benzoic acid). No benzyl ester of 4-hydroxybenzoic acid could be detected in the reaction mixture (GC). The amount of benzyl alcohol was below 1% of the organic phase.

Example 5

5-Chlorovaleronitrile

A mixture of sodium cyanide (1.96 g, 40 millimoles, Aldrich, 95+%), sodium iodide (0.30 g, 2 millimoles, Aldrich, 98%) and water (199.23 g) was prepared in a three-necked 500 mL flask. The organic phase consisting of 1,4-dichlorobutane (10.17 g, 80 millimoles, Aldrich, 97%), Adogen 464 (1.74 g, 4.0 millimoles, Aldrich), and 1,3-dimethoxybenzene (GC standard, 0.68 g, 5 millimoles, Aldrich, 98+%) was introduced into the reactor at 62° C. The organic phase: aqueous phase weight ratio was 1:16. The reaction mixture was stirred mechanically (600 rpm) at 62° C. The pH of the solution was checked from time to time to ensure that it does not decrease as a result of the alkyl chloride hydrolysis or dehydrochlorination. The aliquot taken after 250 minutes after the addition of the organic phase was briefly centrifuged and the organic phase was injected into the GC instrument. The yield of the mono substituted product, 5-chlorovaleronitrile, was 59%. The only other detected product was a disubstituted compound (adiponitrile, below 5%).

Example 6

Adiponitrile

A mixture of sodium cyanide (2.06 g, 42 millimoles, Aldrich, 95+%), sodium iodide (0.30 g, 2 millimoles, Aldrich, 98%) and water (211.01 g) was prepared in a three-necked 500 mL flask and warmed to 65° C. The organic phase consisting of 1,4-dichlorobutane (2.67 g, 21 millimoles, Aldrich, 97%), Adogen 464 (1.76 g, 4.0 millimoles, Aldrich), and 1,3-dimethoxybenzene (GC standard, 0.74 g, 5.7 millimoles, Aldrich, 98+%), and 1,2-dichlorobenzene (2.96 g, solvent, Aldrich, 99%) was introduced into the reactor at 65° C. The organic phase: aqueous phase weight ratio was 1:27. The reaction mixture was stirred mechanically (600 rpm) at 65° C. The pH of the solution was checked from time to time to ensure that it did not decrease as a result of the alkyl chloride hydrolysis or dehydrochlorination. The aliquots were taken after every hour of the reaction, briefly centrifuged, and the organic phase was injected into the GC column. The reaction was stopped after 430 minutes from the addition of the organic phase. The yield of the di-substituted product (adiponitrile) was 40%(the measurement took into account its solubility in water) and the yield of monosubstituted product was 16%.

Example 7

1,3-Dimethoxybenzene

An aqueous phase consisting of resorcinol (2.20 g, 20 millimoles, Lancaster, 99%), tetrabutyl-ammonium bromide (1.30 g, 50% w/w solution in water, 2 millimoles, Sachem 821 East Woodward, Austin, Tex. 78704), sodium hydroxide (5.01 g, 50% w/w solution in water, 60 millimoles, Aldrich), and water (248.83 g) was treated with a mixture of dimethyl sulfate (12.63 g, 100 millimoles, Aldrich, 99+%) and 3-methylanisole (GC standard, 0.750 g, 6 millimoles, Aldrich, 99%). The excess molar concentration of sodium hydroxide was 0.5. The organic phase:aqueous phase weight ratio was 1:18. The two phase system was stirred mechanically (600 rpm, a calibrated photo-tachometer) at room temperature (25° C.). Aliquots were taken after 0, 1, 3, 5, 8, 12, and 18 minutes after the addition of the alkylating agent. When aliquots were taken the pH of the reaction mixture was checked to determine if the hydrolysis of dimethyl sulfate caused the system to become acidic. After 5 minutes of the reaction, the pH became acidic and the reaction mixture was treated with an additional amount of sodium hydroxide solution (3.50 g, 50 w/w solution in water). Aliquots were briefly centrifuged, the phases were separated and the organic phase was injected into the GC column. The yield of 1,3-dimethoxybenzene based on the limiting reactant (resorcinol) was 47% after 12 minutes of reaction.

Example 8

Allyl Phenyl Ether

A mixture comprising phenol (1.882 g, 20 millimoles, Aldrich, 99+%), sodium hydroxide (2.001 g 50% w/w water solution, 24 millimoles, Aldrich), and water (204.61 g) was prepared in the three-necked 500 mL flask and warmed up to 33° C. The excess molar concentration of sodium hydroxide was 0.20. The organic phase consisting of allyl bromide (7.34 g, 60 millimoles, Aldrich, 99%), 3-methylanisole (GC standard, 0.641 g, 5 millimoles, Aldrich, 99%), and Adogen 464 (0.43 g, 1 millimole, Aldrich) was added to the aqueous phase and the two phase system was stirred mechanically (600 rpm, a calibrated photo-tachometer) for 10 minutes at 33° C. The organic phase:aqueous phase weight ratio was 1:25. The aliquots were taken every few minutes to determine the moment when the reaction was complete. After a brief centrifugation the phases were separated and the organic phase of each aliquot was injected into the GC instrument. The reaction was over after 5 minutes and the yield of allyl phenyl ether based on phenol was above 90%. Very small additional peaks (the total yield below 3%) could be detected in the chromatograms.

Example 9

Benzyl Chloroacetate

A mixture consisting of sodium chloroacetate (2.344 g, 20 millimoles, Aldrich, 98%), sodium iodide (0.152 g, 1 millimole, Aldrich, 98%) and water (249.3 g) was introduced to a three-necked 500 mL flask. The organic phase consisting of benzyl chloride (10.139. g, 80 millimoles, Aldrich, 97%), durene (GC standard, 0.781 g, 6 millimoles, Aldrich, 98%), and Adogen 464 (0.900 g, 2 millimoles, Aldrich) was added to the aqueous phase and the two phase system was stirred mechanically (600 rpm, a calibrated photo-tachometer) for about seven hours at 45° C. The organic phase:aqueous phase weight ratio was 1:21. The aliquots were taken at 0, 30, 97, 186, 300 and 400 minutes after the addition of the organic phase. After a brief centrifugation the phases were separated and the organic phase of each aliquot was injected into the GC instrument. The yield of benzyl chloroacetate based on the limiting reactant (sodium chloroacetate) was 55%, the conversion of the chloroacetate anion was 67%. Benzyl chloroacetate was accompanied by small quantities of benzyl iodide and benzyl alcohol and an unidentified product. Its yield was above 10%.

Example 10

Benzoyl Cyanide

A mixture of benzoyl chloride (1.85 g, 13 millimoles, Aldrich, 99%) and Aliquat 336 (0.043 g, 0.1 millimoles) was added to a cooled one neck 250 mL flask containing an aqueous solution consisting of sodium cyanide (0.49 g, 10 millimoles, Aldrich, 95+%), sodium hydroxide (0.135 g, 3 millimoles, Merck; the purpose of adding sodium hydroxide is to prevent acidification of the system as a result of benzoyl chloride hydrolysis), and water (50.17 g). The organic phase:aqueous phase weight ratio was 1:26. The reaction mixture was stirred magnetically at 7–8° C. After 5 minutes an aliquot of the mixture (0.50 g) was taken and mixed with 0.25 g of 5% w/w solution of durene in chlorobenzene. The organic phase was injected into the GC instrument. Benzoyl cyanide is the only product (no "dimer" could be detected). The yield is 95%. No benzoyl cyanide was present in the reaction mixture after 5 minutes when the similar reaction was performed without the phase transfer catalyst. Another blank experiment showed that rather insignificant amounts of benzoic acid (less than 10% after 40 minutes at room temperature) were formed from benzoyl chloride within time limits of the benzoyl cyanide formation.

Example 11

Ethyl Phenoxyacetate

The three-necked 500 mL flask was filled with phenol (1.89 g, 20 millimoles, Aldrich, 99+%), sodium hydroxide (1.76 g, 50% w/w solution in water, 22 millimoles, Aldrich), sodium iodide (0.18 g, 1 millimole, Aldrich, 98%), and water (196.78 g) and immersed in the water bath kept at 60° C. The excess molar concentration of sodium hydroxide was 0.10. The mixture was stirred mechanically at 600 rpm. Next, the organic phase consisting of ethyl chloroacetate (9.84 g, 80 millimoles, Aldrich, 99%), Aliquat 336 (0.834 g, 2 millimoles, and 3-methylanisole (GC standard, 0.490 g, 4 millimoles, Aldrich, 99%) was introduced into the flask. The organic phase: aqueous phase weight ratio was 1:18. The stirring was continued at 60° C. for several hours. The aliquots were taken every 60–90 minutes and briefly centrifuged. The organic phase was injected into the GC instrument. The yield of ethyl phnoxyacetate after 390 minutes retention time was 18%.

Example 12

Anisole

A mixture of phenol (6.60 g, 70 millimoles, Aldrich, 99+%), 3-methylanisole (GC standard, 1.20, 10 millimoles, Aldrich, 98%), Adogen 464 (1.50 g, 3.5 millimoles, Aldrich), and water (683 g) was introduced into a 1000 mL. pressure reactor (Ace Glass, Inc. 1430 Northwest Boulevard, Vineland, N.J. 08362) immersed in a water bath kept at a constant temperature of 40° C. (Prior to the reaction the vessel was pressure checked with air at 35 psig for 15 minutes to ensure that there were no leaks. The air was evacuated to 40 mm Hg absolute pressure using a water aspirator.) Methyl bromide from a gently warmed cylinder (Aldrich) wrapped with insulation was introduced to the reactor through ¼ in. plastic tubing connected to a gas dispersion frit located at the bottom of the reactor until the total reactor pressure reached 24 psig. The connection between the methyl bromide cylinder and the reactor was closed thus isolating the reactor and the mixture was stirred mechanically at the rate of 600 rpm (the rate of stirring was temporarily checked with a calibrated photo-tachometer from VWR). Next, sodium hydroxide (7.40 g, 50% w/w solution in water, 92 millimoles, Aldrich) was introduced into the reactor. The pressure in the reactor was continuously measured. The mixing was continued for 20 minutes and the pressure decreased steadily until it reached 4.5 psig. Then the residual pressure (excess methyl bromide) was released, the reactor opened, and an organic aliquot was taken. The aliquot was centrifuged briefly and the organic phase was injected into the GC column. Anisole was the only detectable product and its yield based on the limiting reactant phenol was 95%.

Example 13

Benzyl Acrylate

A mixture consisting of sodium acrylate (1.892 g, 20 millimoles, Aldrich, 97%), sodium iodide (0.298 g, 2 millimoles, Aldrich, 98%), and water (200.35 g) was introduced into a three-necked 500 mL flask. The flask was immersed into a water bath kept at 45° C. and the mixture was stirred mechanically (600 rpm, photo-tachometer). Next, an organic phase comprising benzyl chloride (10.128 g, 80 millimoles, Aldrich, 97%), Aliquat 336 (1.29 g, 3 millimoles, Aldrich), butyl acrylate (GC standard, 0.690 g, 5 millimoles, Aldrich, 99+%), and 2,6-di-t-butyl-4-methylphenol (0.045 g, 0.2 millimoles, Aldrich, 99+%) was added to the reactor and the mixture was stirred for 180 minutes at constant temperature. The organic phase:aqueous phase weight ratio was 1:17. The aliquot of the reaction mixture was centrifuged, the phases were separated and the organic phase was injected into the gas chromatographic column. The yield of benzyl acrylate based on the limiting reactant (sodium acrylate) was 59%. The only byproduct detectable in the reaction mixture was benzyl alcohol (less than 3%).

Example 14

Benzyl Acetate

An aqueous phase consisting of sodium acetate (2.46 g, 30 millimoles, Aldrich, 97%), sodium iodide (0.23 g, 1.5 millimoles, Aldrich, 98%) and water (250.36 g) was warmed up in a three-necked 500 mL flask to 40° C. Next, a mixture of benzyl chloride (15.19 g, 120 millimoles, Aldrich, 97%), Adogen 464 (1.33 g, 3 millimoles, Aldrich), and durene (0.94 g, 7 millimoles, Aldrich, 98%) was added to the reactor. The organic phase:aqueous phase weight ratio was 1:14. The two phase mixture was stirred mechanically (600 rpm) at 40° C. for 335 minutes. The aliquot of the reaction mixture was centrifuged, the phases were separated and the organic phase was injected into the gas chromatographic column. The yield of benzyl acetate based on the limiting reactant (sodium acetate) was 50%. The byproducts present in the reaction mixture were benzyl alcohol (3%) and benzyl iodide (trace).

When the same reaction was performed for 240 minutes at 60° C. (3 millimoles of sodium iodide and 6 millimoles of Aliquat 336) the yield of benzyl acetate based on sodium acetate was 57%, the conversion of sodium acetate was 89%, and the reaction mixture contained a significant quantity of benzyl alcohol (above 10%).

Example 15

1-Nitropropane

A mixture comprising sodium nitrite (1.383 g, 20 millimoles, Aldrich, 99%), potassium carbonate (0.687 g, 5 millimoles, Aldrich, 99%) and water (151.04 g) was prepared in the three-necked 500 mL flask and warmed up to 4° C. The organic phase consisting of 1-bromopropane (9.901 g, 80 millimoles, Aldrich, 99%), durene (GC standard, 0.424 g, 3 millimoles, Aldrich, 99%), and Adogen 464 (0.81 g, 2 millimoles, Aldrich) was added to the aqueous phase and the two phase system was stirred mechanically (600 rpm, a calibrated photo-tachometer) at 40° C. After 60 minutes of the reaction, the aliquot was taken, briefly centrifuged and a sample of the organic phase injected into the GC. The yield of 1-nitropropane was 30% based on sodium nitrite.

Example 16

Butyl Acrylate

Sodium acrylate (30 mmoles=2.82 g) was dissolved in water (300.04 g) in the three-necked 500 mL flask. The reaction flask was immersed in a water bath at 70.5° C. and stirred mechanically (about 600 rpm). Then, a mixture consisting of butyl bromide (120 mmoles=16.46 g), Aliquat 336 (3 mmoles=1.32 g), durene (chromatographic standard, 5 mmoles=0.67 g, Aldrich, 98%) and traces of hydroquinone and DTBMP (2,6-di-tert-butyl-4-methylphenol, Aldrich 99+%, to prevent polymerization) was added to the water phase. The organic phase:aqueous phase weight ratio was 1:16. The reaction mixture was stirred mechanically at 69° C. (measured inside the flask) at the rate of 620 rpm (measured periodically). Aliquots of the organic phase were taken after 0, 10, 30, 60, 120 and 180 minutes from the moment of mixing both phases. The only detectable product is butyl acrylate with a yield above 60% based on acrylate anion.

Example 17

Ethyl Trichloroacetate

A solution of trichloroacetic acid (3.33 g, 20 millimoles, Sigma, 99.0+%) in water (171.02 g) was introduced into a three-necked 500 mL flask and warmed up to 60° C. when mechanically stirred (600 rpm). Next, the organic phase consisting of diethyl sulfate (15.49 g, 100 millimoles, Aldrich, 99+%), Adogen 464 (0.90 g, 2 millimoles, Aldrich), and durene (chromatographic standard, 0.652 g, 5 millimoles. Aldrich, 98%) was added to the flask. The organic phase:aqueous phase weight ratio was 1:10. Since diethyl sulfate decomposes in water, the reaction mixture was stirred at 60° C. for 30 minutes. Then, the reaction was stopped and an aliquot of the organic phase was centrifuged to remove the aqueous phase and injected into the gas chromatographic column. The yield of ethyl trichloroacetate based on the limiting reactant (trichloroacetic acid) was 15%. No other products were present in the chromatogram.

Example 18

Benzyl Phenyl Ether

Phenol (2.836 g, 30 millimoles, Aldrich, 99+%), sodium hydroxide (1.411 g, 35 millimoles, Merck, 97%), and sodium iodide (0.433 g, 3 millimoles, Aldrich, 98%) were dissolved in water (299.19 g). The excess molar concentration of sodium hydroxide of was 0.166. The aqueous phase was introduced into a 3-neck 500 mL reactor immersed in the water bath at 50° C. The mixture consisting of benzyl chloride (3.930 g, 31 millimoles, Aldrich, 97%), Aliquat 336 (2.597 g, 6 millimoles, Aldrich), durene (0.693 g, 5 millimoles, Aldrich, 98%), and toluene (15.02 g, J. T. Baker, ultra-pure). The organic phase:aqueous phase weight ratio was 1:14. The two phase mixture was stirred mechanically (600 rpm) at 50° C. for 90 minutes. The aliquot of the reaction mixture was centrifuged, the phases were separated and the organic phase was injected into a GC column. The yield of benzyl phenyl ether based on the limiting reactant (phenol) was 70%. No byproducts could be detected in the chromatograms representing the reaction mixture.

Example 19

Butyl Phenyl Ether

A solution of phenol (2.86 g, 30.4 millimoles, Aldrich, 99+%), sodium hydroxide (1.34 g, 33.5 millimoles, Merck, 97%) and water (299.69 g) was introduced into the three-necked, 500 mL reactor and warmed up to 65° C. The excess molar concentration of sodium hydroxide of was 0.1 This aqueous solution was mechanically stirred (610 rpm) and treated with an organic phase consisting of 1-bromobutane (15.27 g, 111.4 millimoles, Aldrich, 99+%), durene (GC standard, 0.73 g, 5.4 millimoles, Aldrich, 98%), and Aliquat 336 (1.30 g, 3 millimoles, Aldrich). The organic phase:aqueous phase weight ratio was 1:17. The reaction mixture was stirred at 65° C. for 30 minutes. An aliquot of the organic phase was injected into the gas chromatographic column. The yield of butyl phenyl ether based on the limiting reactant (phenol) was 92%.

Example 20

Varying Amount of Base

Phenol (1.88 g, 20 millimoles, Aldrich, 99+%) accompanied by varying quantities of sodium hydroxide (50% solution in water, Aldrich) was dissolved in water (200 g). In each experiment the quantities of sodium hydroxide were:

A. 1.62 g (40 millimoles, 100% excess)
B. 0.92 g (23 millimoles, 15% excess)
C. 0.83 g (20.75 millimoles, 3.75% excess).

The aqueous phase was reacted (600 rpm, 32° C., 500 mL three-necked reactor) with the organic phase consisting of allyl bromide (7.26 g, 60 millimoles, Aldrich, 99%), Adogen 464 (0.81 g, 2 millimoles, Aldrich), and 3-methylanisole (0.67 g, 5.6 millimoles, Aldrich, 99%). The yields of allyl phenyl ether were:

| Rxn time | A | B | C |
| --- | --- | --- | --- |
| 3 minutes | 54.6 | 48.9 | 41.9 |
| 8 minutes | 90.3 | 84.7 | 74.4 |
| 15 minutes | 99.5 | 100 | 93.4 |

Example 21

Allyl Phenyl Ether Using Excess of Phenolate

A mixture comprising phenol (5.64 g, 60 millimoles, Aldrich, 99+%), sodium hydroxide (6.41 g 50% w/w water solution, 80 millimoles, Aldrich), and water (124.63 g) was prepared in the three-necked 500 mL flask and warmed up to 32° C. The organic phase consisting of allyl bromide (2.42 g, 20 millimoles, Aldrich, 99%), 3-methylanisole (GC standard, 0.65 g, 5 millimoles, Aldrich, 99%), and Adogen 464 (0.41 g, 1 millimole, Aldrich) was added to the aqueous phase and the two phase system was stirred mechanically (600 rpm, a calibrated photo-tachometer) at 32° C. The aliquots were taken every few minutes. After a brief centrifugation the phases were separated and the organic phase of each aliquot was injected into the GC instrument. After 30 minutes of the reaction allyl bromide constituted about 2.5% of the organic phase and the yield of allyl phenyl ether (based on allyl bromide) was above 65%.

Example 22

Allyl Phenyl Ether from an Authentic Waste Containing Phenol

An authentic waste mixture (colorless, 20.10 g, about 200 millimoles) from a Resorcinol production waste stream supplied by Indspec Chemical of Pittsburgh, Pa., comprising phenol (80+/−3%), resorcinol (7+/−2.5%), m,p-cresol (8+/−1.5%), o-cresol (<2%), and water (<2%) was mixed with water (181.56 g) and sodium hydroxide (23.56 g, 295 millimoles, 50% w/w water solution, Aldrich). The yellowish mixture was introduced into a three-necked 500 mL flask. An organic phase consisting of allyl bromide (38.28 g, 310 millimoles, Aldrich, 99%), 3-methylanisole (GC standard, 2.49 g, 20 millimoles, Aldrich, 99%), and Adogen 464 (4.08 g, 10 millimoles, Aldrich) was added to the aqueous phase and the two phase system was stirred mechanically (600 rpm, a calibrated photo-tachometer) at 28° C. After 15 minutes of reaction time an aliquot was taken, briefly centrifuged and the organic phase injected into the GC column. Only O- and C-alkylation products of phenol could be detected in the reaction mixture. The yield of the allyl phenyl ether was 75% based on the limiting reactant phenol.

Although illustrated and described herein with reference to certain specific embodiments and examples, the present invention is nevertheless not intended to be limited to the details shown. Rather, the claims should be read to include various modifications within the scope and range of equivalents of the claims, without departing from the spirit of the invention.

What is claimed:

1. A method for making an organic product comprising the step of contacting an aqueous solution providing an aqueous phase and having a low concentration of a chemical species comprising a nucleophile selected from the group consisting of cyanide, thiocyanate, cyanate, carboxylate, sulfonate, carbonate, nitrite, azide, and iodide with: (1) an organic phase consisting of an electrophile, wherein said electrophile is an alkylating agent or an acylating agent presented in an amount to achieve an organic phase:aqueous phase ratio of 1:3 or less by weight; and (2) a phase transfer catalyst for transferring said nucleophile from said aqueous phase to said organic phase or to the aqueous-organic interface to enhance a nucleophilic substitution reaction in said organic phase or in the aqueous-organic interface between said nucleophile and said electrophile to form said organic product, wherein said low concentration of chemical species comprising a nucleophile is between 0.001 and 25 wt. % in said aqueous phase, wherein said organic product is selected from the group consisting of benzyl cyanide, alkyl cyanides, acyl cyanides, alkyl thiocyanates, acyl thiocyanates, alkyl cyanates, acyl cyanates, carboxylic esters, carboxylic anhydrides, alkyl sulfates, alkyl carbonates, nitroalkanes, alkyl azides, acyl azides, alkyl iodides, and acyl iodides, and wherein said contacting is performed at a temperature between 0 and 80° C.

2. The method in accordance with claim 1, wherein said nucleophile is carboxylate or a carboxylate derivative, said electrophile is an alkylating agent, and said organic product comprises a carboxylic ester.

3. The method in accordance with claim 1, wherein said nucleophile is cyanide, said electrophile is benzyl chloride, and said organic product comprises benzyl cyanide.

4. The method in accordance with claim 1, wherein said electrophile is an acyl halide selected from the group consisting of benzoyl chloride and stearoyl chloride.

5. The method in accordance with claim 1, wherein said low concentration is between 0.001 weight percent and 10 weight percent of said chemical species.

6. The method in accordance with claim 1, wherein said low concentration is between 0.001 weight percent and 5 weight percent of said chemical species.

7. The method in accordance with claim 1, wherein said low concentration is between 0.001 weight percent and 1 weight percent of said chemical species.

8. The method in accordance with claim 1, wherein said phase transfer catalyst is selected from the group consisting of a quaternary ammonium salt, a quaternary phosphonium salt, quaternary arsonium salt, a crown ether, cryptate, a polyethylene glycol, and derivatives thereof.

9. The method in accordance with claim 1, wherein said phase transfer catalyst is a quaternary ammonium salt selected from the group consisting of methyltricaprylylammonium chloride, and tetrabutylammonium bromide or a tertiary amine such as Tris(3,6-dioxaheptyl)amine.

10. The method in accordance with claim 1, wherein said nucleophile is carboxylate, cyanide, or a derivative thereof.

11. The method in accordance with claim 1, wherein said electrophile is an alkylating agent that is an alkyl halide.

12. The method in accordance with claim 1, wherein the nucleophile comprises a target anion.

13. The method in accordance with claim 1, wherein the contacting step further comprises contacting the aqueous solution with a co-catalyst for further enhancing the reaction rate in the organic phase.

14. The method in accordance with claim 13, wherein the co-catalyst is selected from the group consisting of sodium Iodide, potassium iodide, lithium iodide and ammonium iodide.

15. The method in accordance with claim 1, wherein the organic phase:aqueous phase ratio is 1:5 or less by weight.

16. The method in accordance with claim 1, wherein the organic phase:aqueous phase ratio is 1:10 or less by weight.

17. The method in accordance with claim 1, wherein the organic phase:aqueous phase ratio is 1:20 or less by weight.

18. The method in accordance with claim 1, wherein said alkylating agent is selected from the group consisting of benzyl chloride, an allyl bromide, and epichlorohydrin.

* * * * *